United States Patent [19]
Gustavsson et al.

[11] Patent Number: 5,643,480
[45] Date of Patent: Jul. 1, 1997

[54] FIELD OF THE INVENTION

[75] Inventors: Magnus Peter Mikael Gustavsson, Halmstad; Ronny Kent Hagman, Göteborg, both of Sweden

[73] Assignee: Nordica S.p.A., Trevignano, Italy

[21] Appl. No.: 338,488

[22] PCT Filed: May 19, 1993

[86] PCT No.: PCT/SE93/00453
§ 371 Date: Nov. 18, 1994
§ 102(e) Date: Nov. 18, 1994

[87] PCT Pub. No.: WO93/23968
PCT Pub. Date: Nov. 25, 1993

[30] Foreign Application Priority Data
May 19, 1992 [SE] Sweden ............ 9201585

[51] Int. Cl.$^6$ ............ H05B 3/34; H01M 10/50
[52] U.S. Cl. ............ 219/211; 429/120
[58] Field of Search ............ 219/211, 212, 219/549, 528; 429/120, 127

[56] References Cited

U.S. PATENT DOCUMENTS

| | | | |
|---|---|---|---|
| 3,023,259 | 2/1962 | Coler et al. | 429/127 |
| 3,623,471 | 11/1971 | Bogue | 429/127 |
| 3,768,156 | 10/1973 | Caird et al. | 219/211 |
| 4,092,464 | 5/1978 | Dey et al. | 429/127 |
| 4,195,121 | 3/1980 | Peterson | 429/127 |
| 4,701,279 | 10/1987 | Kawaguchi et al. | 252/511 |
| 4,703,754 | 11/1987 | Ibbott | 429/127 |
| 4,761,541 | 8/1988 | Batliwalla et al. | 219/528 |

FOREIGN PATENT DOCUMENTS

| | | |
|---|---|---|
| 0138424 | 9/1984 | European Pat. Off. |
| 0158410 | 1/1985 | European Pat. Off. |
| 0235454 | 12/1986 | European Pat. Off. |
| 0287294 | 4/1988 | European Pat. Off. |
| 3928043 | 8/1989 | Germany . |
| 2-253571 | 10/1990 | Japan . |
| 530145 | 8/1971 | Switzerland . |
| 8701549 | 8/1986 | WIPO . |
| 9003713 | 9/1989 | WIPO . |

OTHER PUBLICATIONS

Patent Abstracts of Japan, vol. 14, No. 580, E-1017, abstract of JP, A, 2-253571 (Japan Storage Battery Co Ltd), 12 Oct. 1990 (Oct. 12, 1990).

*Primary Examiner*—Teresa J. Walberg
*Assistant Examiner*—Sam Paik
*Attorney, Agent, or Firm*—Ladas & Parry

[57] ABSTRACT

An electric heating device (34) in which is included an electric energy source (45) which is designed as a thin film battery (45). The heating device also includes a resistor heating unit (40) comprising a first material stratum (40) consisting of an electrically conductive polymer material with PTC properties. The resistor heating unit (40) and the electric energy source (45) are disposed adjacent to one another and form a composite unit in which the major surfaces of the first material stratum (40) and thin film battery (45), respectively, face towards one another. Electrodes (42, 43) are connected, by the intermediary of a switch (48), to the poles of the battery (45) and to the resistor heating unit (40).

18 Claims, 6 Drawing Sheets

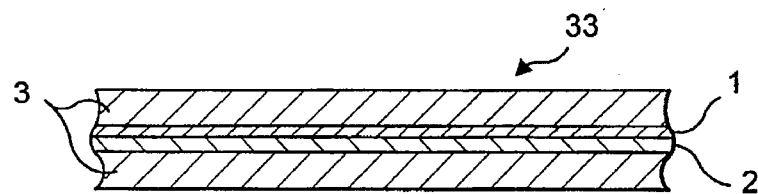
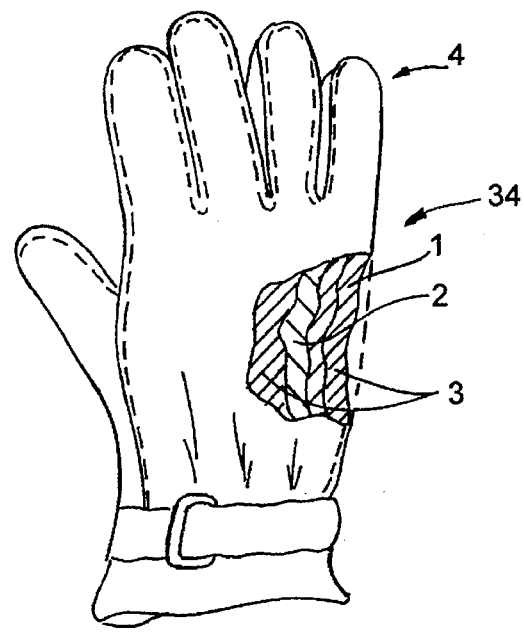
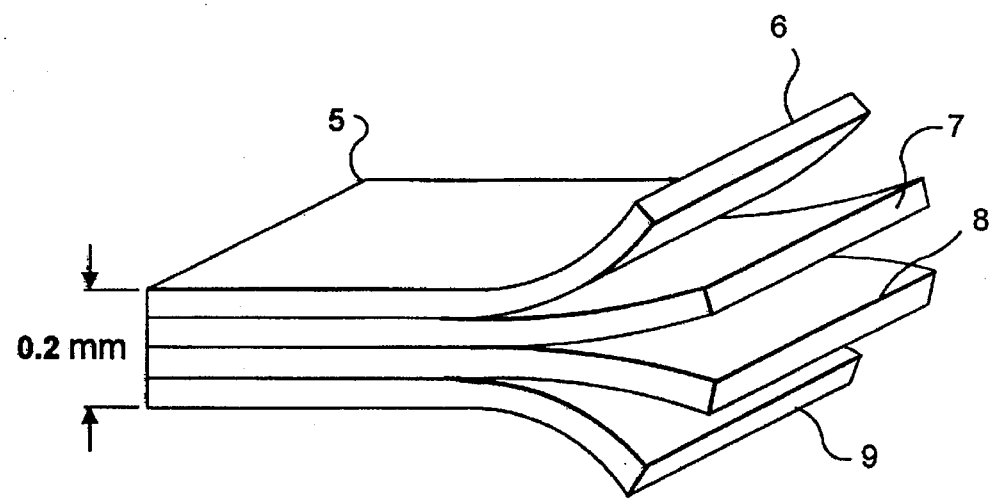

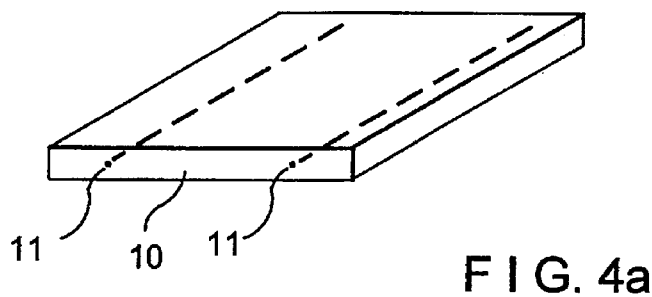
F I G. 4a
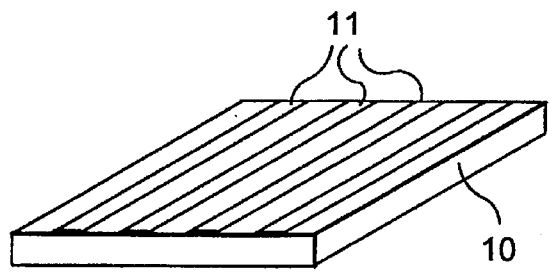
F I G. 4b
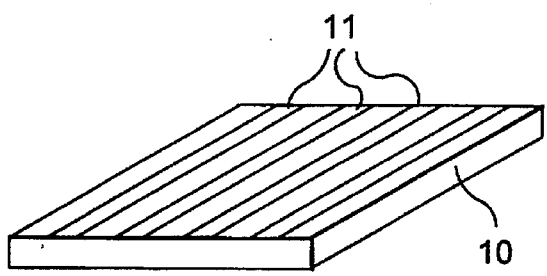
F I G. 4c
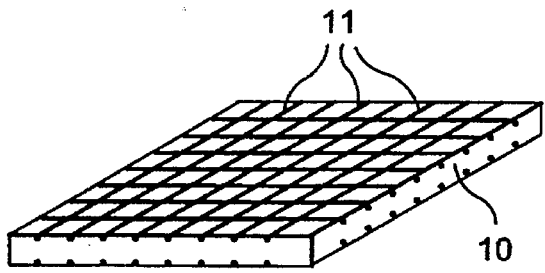
F I G. 4d

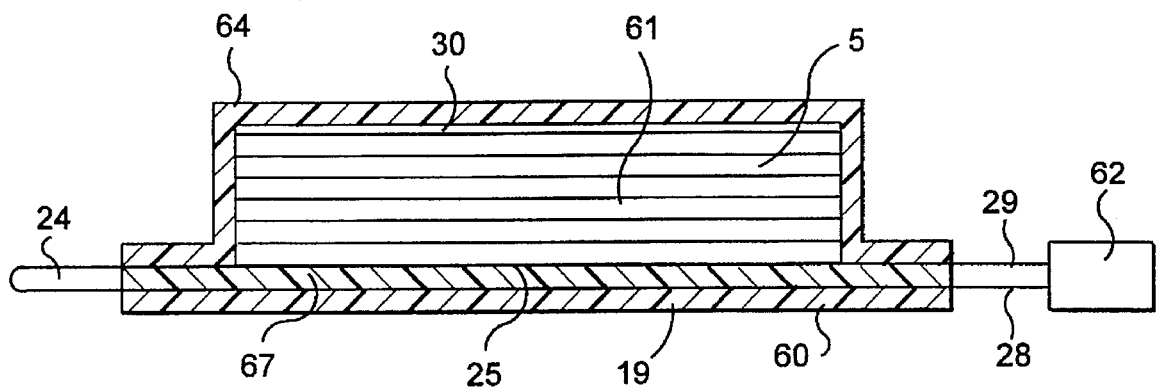
F I G. 8
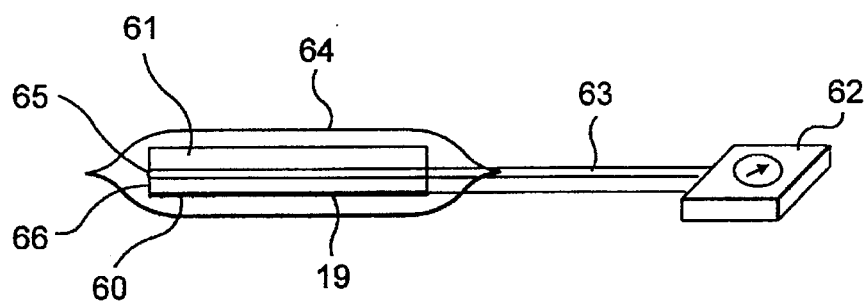
F I G. 9

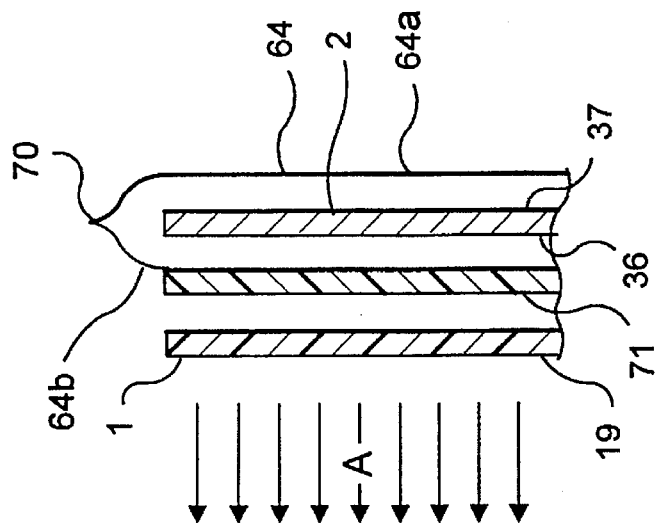
FIG. 10c
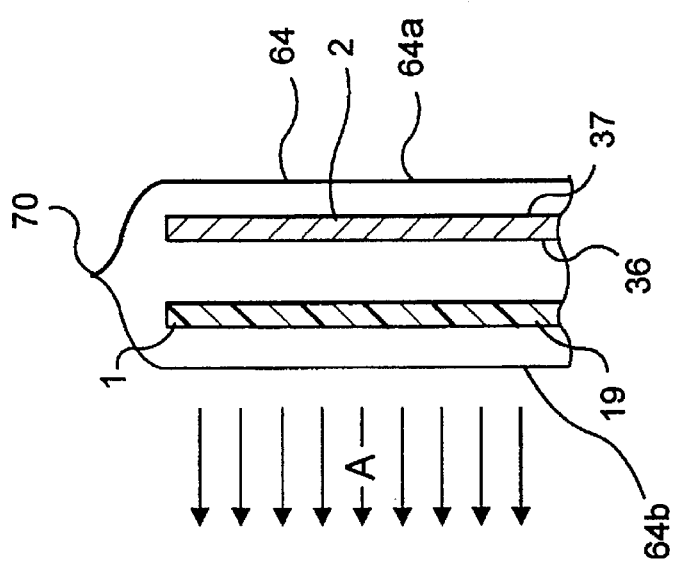
FIG. 10b
FIG. 10d
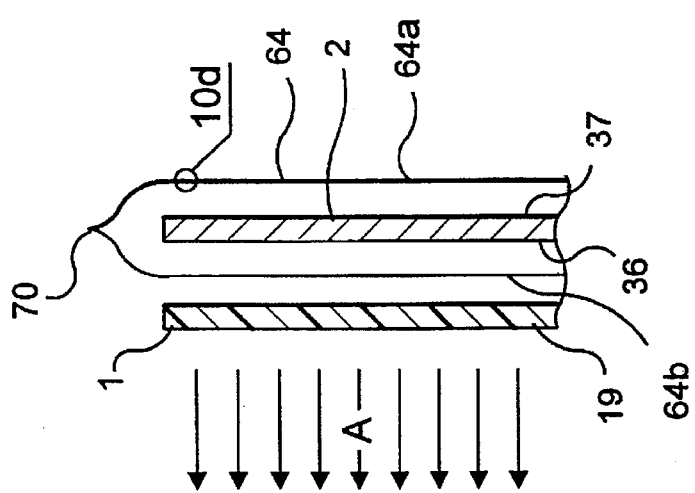
FIG. 10a
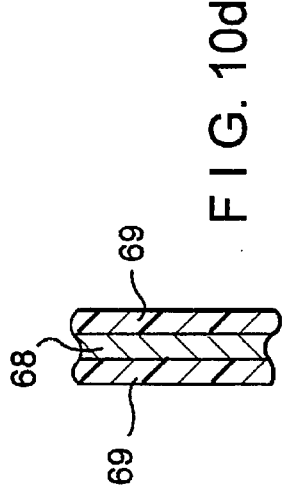

FIELD OF THE INVENTION

FIELD OF THE INVENTION

The present invention relates to an electric heating device in which electrical resistor heating elements are incorporated with a layer or substrate of material.

BACKGROUND AND PRIOR ART

Within many fields of activity, it is desirable to heat different parts of the body, for example for medical purposes or for reasons of comfort. One example is the heating of joints, hands and other parts of the body of rheumatism sufferers. Another example is within the areas of sports and leisure activities where proposals have been put forward for heated gloves, shoe inlays and other items of clothing as well as sleeping-bags.

It is also desirable in the art to devise containers which, on transport or power failure, maintain an elevated temperature in their storage space. Similarly, there are needs for substrates which, on transport or power failure, maintain an elevated temperature, for example to avoid the risk that the temperature falls in accumulators or batteries placed on the substrates—which could lead to a reduction in the quantity of energy which can be extracted from them.

To cover these needs numerous solutions have been proposed in the art, these all being based on electric heating with the aid of various resistor heating elements and electric energy sources, normally dry cell batteries. As examples of this known technology, mention might be made of Swedish patent application No. 8402743-2 which describes a glove intended for rheumatics with inlaid resistor wires and a current source so as to develop a thermal effect exceeding 25 W in the glove.

In a corresponding manner, Swedish patent application No. 8404783-6 describes a medical undergarment with inlaid resistor heating elements and a current source in the form of a battery. Electrically heated shoe inlays are described, for instance, in the two German specifications DE-A-3 904 603 and DE-C-4 000 259. These shoe inlays have inlaid resistor heating elements which are connectable to a battery or other source of electric energy. In both cases, the resistor heating elements are in the form of printed conductor paths on a base consisting of plastic or other non-conductive material. In both cases, the heating proper is also controlled by means of electric circuit connections so as to as avoid overheating.

As was mentioned above, it is known in the leisure-time sector to make use of electrically heated sleeping-bags or garments. One example is disclosed in US-A-3,443,066 which describes a sleeping-bag or other clothing garment of flexible, thermally insulating material with inlaid resistor heating wires and batteries for electric power supply.

In automotive engineering, similar ideas have been employed, for example to provide heating elements for vehicle seats, an employment which necessitates a degree of give in the inlaid resistor heating elements. One example of this technique is described in SE-B-434 204 (7713250-4), in which the give or extensibility has been achieved by making the inlay of meandering loops of resistor heating wires or tapes in a layer in the padding material of the seat.

Yet a further a example of textile material which can be heated electrically is to be found in US-A-4,845,343 in which the resistor wires have been woven into the fabric structure proper.

All of these prior art devices for heating larger or smaller parts of the body of a patient or general user suffer from numerous common drawbacks. One such drawback is that the prior art resistor heating elements consume considerable quantities of power and are, therefore, expensive in operation. Another drawback is that the possibilities of regulating the heating effect locally, i.e. within a limited part of the body are poor—in other words the user must choose between either a heating effect which gives satisfactory heating of the coldest part of the body which at the same time results in overheating of other parts of the body, or a heating effect which provides comfortable heating of the major part of the body but insufficient heating within certain other parts of the body. A further drawback inherent in many of the prior art devices is that they require separate accumulators whose capacity is often reduced at low temperatures, since they must be carried at relatively unprotected positions in the wearer's clothing. Moreover, the separate accumulators must be carried in some type of belt or the like which may prove unwieldy. Another drawback is that some type of external thermostat is necessary in order to be able to obtain a determined average temperature.

SUMMARY OF THE INVENTION

One object of the present invention is, therefore, to realize an electric heating device, for example designed as a panel, a laminate, a band, a container etc, in which device one or more of the drawbacks inherent in prior art technology have been obviated. For example, the device according to the present invention should be suitable to be included in a garment.

A further object of the present invention is to realize a device, an arrangement or an article, for example a garment of clothing, of a design which entails that the heating effect varies locally in response to the local heating requirement.

Yet a further object of the present invention is to render the heating device so thin and flexible that it can be inlaid between two textile layers in a garment of clothing or the like without the appearence or other properties thereof being appreciably altered. Still a further object of the present invention is to devise automatic regulation of the average temperature without the need of an external thermostat. Yet a further object of the present invention is to realize a heating device which includes an electric power source which cooperates with a heating element included in the heating device so as to avoid or counteract the eventuality that the available portion of the capacity of the power source is reduced as a result of cooling of the energy source and, instead, even to increase the available capacity of the energy source in that heat generated in the immediate proximity of the energy source raises the temperature of the energy source. Still a further object of the present invention is to realize reflection of heat towards the energy source by particular placing of the energy source.

These and other objects of the present invention will be attained if the heating device is constituted as a thin film battery formed as a composite unit with resistor heating means combined with a substrate layer of material.

The heating element according to the invention consists of a polymer material with so-called PTC properties (Positive Temperature Coefficient), in particular an electrically conducted thermoplastic material such as conductive, butyl inoculated polyethylene.

The thin film accumulator may advantageously be of the lithium type and have a number of mutually stratified layers including a lithium layer, a polymer electrolyte layer, a vanadinoxide composite layer and a conductor layer.

Electrode material most suitably consisting of a conductor material is united with the heating element by casting, screen printing, gluing with electrically conductive glue or vacuum coating in a suitable pattern so as to make possible electric connection to the thin film battery.

A control circuit may be provided as a conductive path with a connected switch between the two poles of the battery, but is preferably a control circuit with circuit elements for sensing and controlling the battery and possibly also limiting activation time.

The expression "garment" is here taken to signify not only clothing garments such as gloves, waistcoats and the like, but also shoe inlays, sleeping-bags or seat heaters or cushions, for example for leisure time activity purposes.

DETAILED DESCRIPTION OF PREFERRED EMBODIMENTS

The present invention will now be described in greater detail hereinbelow, with particular reference to the accompanying drawings which show embodiments of the present invention. In the accompanying drawings:

FIG. 1 shows a section through one embodiment of an assembly for use in a heating device according to the present invention;

FIG. 2 shows an example of a garment which is designed according to the present invention;

Figure 5:
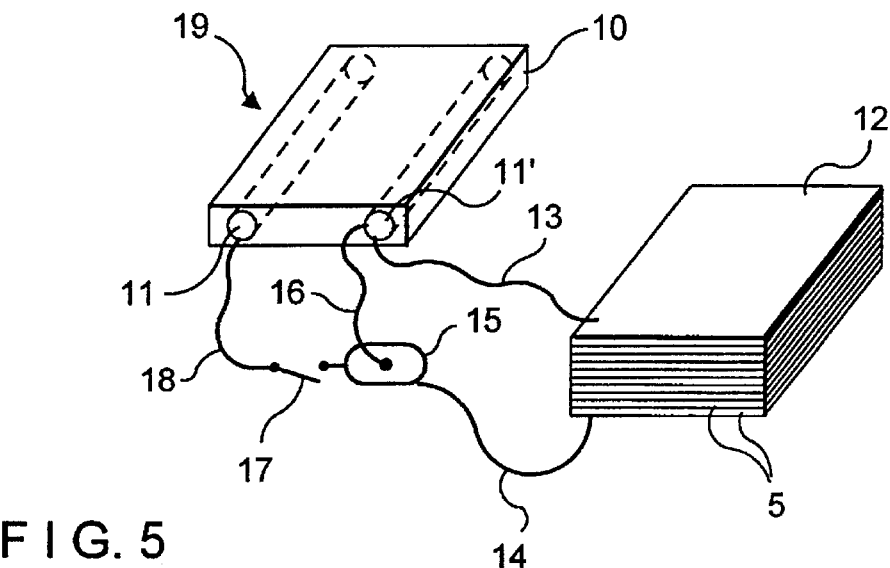
Figure 6A:
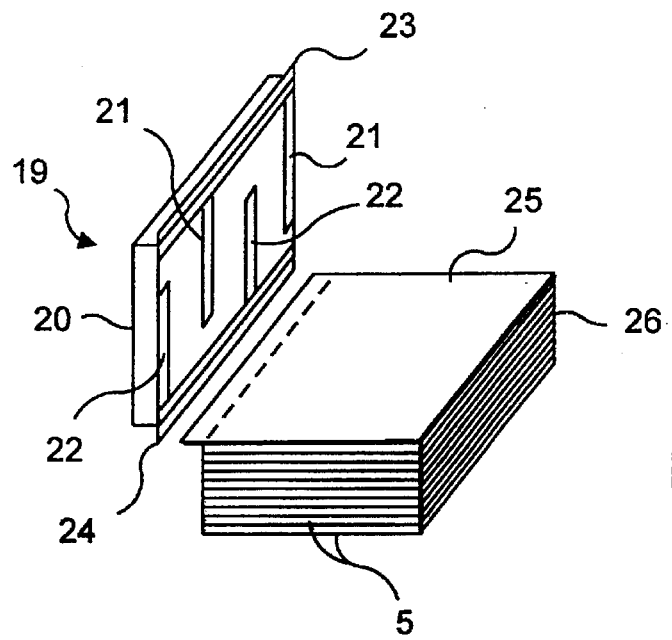
Figure 7A:
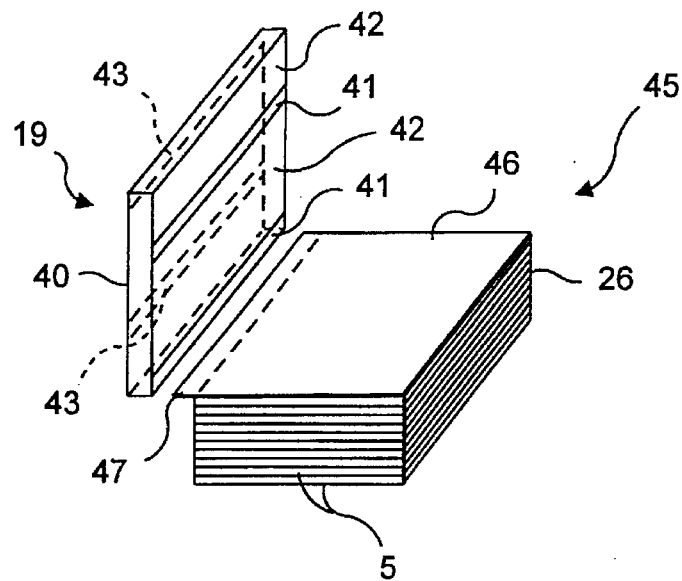

FIG. 3 schematically illustrates a preferred thin film accumulator for use in the present invention;

FIGS. 4a–d show four examples of different methods of uniting electrode material and heating foil material;

FIG. 5 schematically illustrates a first example of how the heating foil material and thin film accumulator may be united;

FIGS. 6a,b schematically illustrate a second example of how the heating foil material and thin film accumulator may be united;

FIGS. 7a,b schematically illustrate a third example of how heating foil material and thin film accumulator may be united;

FIGS. 8–9 schematically illustrate further examples of heating units which may be used in practical application of the present invention; and FIGS. 10a–d schematically illustrate examples of heating units provided with a heat reflecting layer.

FIG. 1 schematically shows a section through one embodiment of the material (an aggregate consisting of several strata) 33 for use in an electric heating device 34 (cf. FIGS. 2 and 9) according to the present invention as described hereinbelow, for example in a garment, a container, an underlay blanket for accident victims, and so on. The aggregate is formed from, or contains, at least a first stratum 1 which consists of or includes at least one layer of an electrically conductive polymer with PTC properties. The first stratum 1 is disposed adjacent and, as a rule, connected to a second stratum 2 included in the aggregate and consisting of a thin film battery 5 thin film accumulator 5. As is apparent from the embodiment illustrated in FIG. 1, the aggregate generally includes protective layers 3 disposed on either side of the two strata 1, 2 and consisting, for example, of plastic material, metal such as metal foil or textile material, or of a combination of two or more of these materials. The structure of the first, second and third strata 1,2 and 3 will be described in greater detail hereinbelow.

FIG. 2 shows one example of an application of the present invention in which the device 34 is designed as a heating glove 4 for, for example, rheumatics.

FIG. 3 shows an example of a thin film battery 5 of a type which is advantageously employed in the practical application of the present invention. In the illustrated embodiment of the thin film battery 5, there is included a lithium layer 6 acting as negative pole, a subjacent polymer composite layer 7 acting as electrolyte, a composite layer 8 acting as positive pole and an electric conductor 9 connected to the composite layer 8. Such a thin film battery is not much thicker than normal letter paper, approx. 0.2 mm. The composite layer 8 consists of a mixture of the electrolyte and a compound which readily entraps lithium ions e.g. vanadium oxide). The lithium ions pass through the electrolyte to the composite layer 8 (the positive pole), while the electrons take the outer path from the lithium layer 6 (the negative pole) to the composite layer 8, i.e. go via an outer load (not shown) and the electric conductor 9. The load constitutes a resistor heating unit and will be described hereinbelow. Both the ions and the electrons are stored in the composite layer 8 and pass back to the lithium layer 6 when the battery is recharged.

Thin film batteries of this type may be purchased from various commercial sources, e.g. the Japanese firm Yuasa Battery, the Canadian firm Hydro Quebec and the Japanese firm Sharp Corporation. Examples of literature in which this type of thin film battery is described is the book published by Elsevier Science Publishers B.V. in 1991 entitled "Chemistry and Energy-I", C. A. C. Segueira (editor) which includes on pp. 153–162, an article written by Jorgen S. Lundsgaard et al "The All-Solid-State Lithium Polymer Electrolyte Battery", and on pp. 163–175 includes an article written by M. A. G. Martins et al "All-Solid-State Thin-Film Polymer Electrolyte Batteries". Another example is Koksbang et al, "Rechargeability and Rate Capability of Polymer Electrolyte Batteries at Room Temperature", Journal of Power Sources, 32 (1990) pp. 175–185.

According to the present invention, the aggregate includes a heating unit in which is included a polymer material with PTC properties. One such particularly suitable material may be obtained from Neste Polymer Compounds AB, Sweden under the designation ET-Semicon CT 6422:70 or 6002:70. These materials are semiconductor thermoplastic materials. Another material which has been utilized in practical tests and which has been obtained from Norells Sweden AB is ET-Semicon CT 8711:70. For connecting these electrically conductive polymer materials 10 with PTC properties, use is made of, for example, cast electrodes (FIG. 4a) an electrode material screen-printed on the polymer layer (FIG. 4b), an electrode material applied to the polymer layer by a vacuum coating method (FIG. 4c), or a partly cast electrode material in the form of a lattice (FIG. 4d). It will be obvious to a person skilled in the art that other connection techniques are also applicable within the framework of the present invention. The lattice-formed electrically conductive electrode material in FIG. 4d is, for example, cast on opposing sides of the polymer layer or connected to the polymer layer by gluing. In FIGS. 4a–d, the polymer layer has been given reference numeral 10 and the electrode material reference numeral 11. In the embodiments illustrated in FIGS. 4b and 4c, the electrode material is, in certain practical applications, connected to the polymer material 10 by a welding process.

A thin film battery of the type which is preferred in the present invention has preferably an average voltage of 2.4 V/polymer layer. In order to obtain a sufficiently high voltage, a number of layers (cf. FIGS. 5–7) are generally laminated. In one expedient embodiment of the present invention, use is made, for example, of ten laminated layers of batteries, in which event a polar voltage of 24 V is obtained. Vacuum technique is employed in one preferred production technology for laminating the various thin film batteries. The different layers are placed on one another, a series connection of the different batteries being obtained in that the positive and negative poles of adjacent batteries are connected to one another, whereafter the layer of batteries is compressed and vacuum sealed. The sealing material consists, in one preferred embodiment, of an aluminum foil whose inside is coated with a layer of an electrically insulating material, for example polyethylene based hot-melt glue.

FIG. 5 schematically illustrates one embodiment of the present invention in which a thin film battery 12 consisting of a plurality of strata is formed from ten mutually superposed and interconnected thin film batteries 5. The composite thin film battery 12 is connected by means of a conductor 13 to one current distributor 11 in the electrically conductive polymer material layer 10. The negative pole of the composite thin film battery 12 is connected by means of a conductor 14 to a charger terminal 15 which, via a switch 17 and a conductor 18, is connected to a second current distributor 11' in the electrically conductive polymer layer 10. Both of the current distributors 11 and 11' are located a distance from one another which is determined by the electric and thermal properties of the polymer layer and by the thermal effect which is to be emitted by the polymer disposed between the current distributors. The current distributors 11,11' and the polymer layer 10 constitute the heating unit 19 of the device.

The charging terminal 15 is, via a conductor 16, connected to the one current distributor 11. When a charger is connected to the charging terminal 15, the positive and negative poles of the device are thereby coupled to corresponding poles in the thin film battery 12 consisting of a plurality of layers.

The electrically conductive polymer layer 10 is, for example, made of ET-Semicon having the commercial designation CT 6002:17. The two electrodes or current distributors 11,11', consist, for example, of wire-like electric conductors which are cast in the polymer layer or are formed from a metal foil or alternatively synthetic metal foil, e.g. ICP material (Intrinsically Conductive Polymers). The wireformed conductors have, in one preferred embodiment, a diameter of 0.9 mm and metal foil thickness of 25 um. The battery 12 consisting of a plurality of strata is cast in or sealed against the surroundings by an electrically insulating, water resistant and water impermeable material in applications in which the thin film batteries 5 are sensitive to moisture. The polymer material layer 10 needs no corresponding protection. In this embodiment in which the heating layer 10 and the thin film accumulator 12 are discrete from one another, the advantage will be afforded that the accumulator can be replaced. In that the electric connections 13,14,16,18 between the battery and the heating unit are conductive, body movements on the part of the wearer will be facilitated.

One major advantage in the employment of an electrically conductive material of the PTC type is that the heating effect can be locally regulated, i.e. colder positions emit more heat than warmer positions. This regulation is automatic as a result of the PTC properties of the material.

Figure 6B:
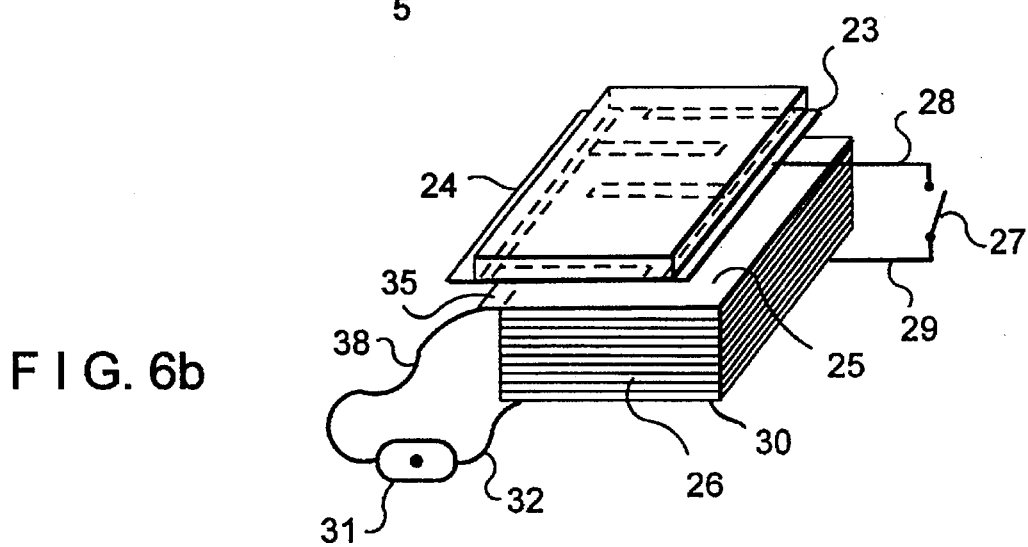

FIGS. 6a and 6b show yet a further embodiment. In this case, the electrically conductive polymer layer 20 with PTC properties included in the heating unit 19 by screen printing has been provided with a first batch of electrodes 21 and a second batch of electrodes 22. The two electrode batches are disposed such that the electrodes are in spaced relationship from one another. The first batch of electrodes 21 has a projecting contact element 23 and the second batch of electrodes 22 has a projecting contact element 24. The heating unit 19 is glued with an electrically insulating glue against the positive pole layer 25 of a thin film battery 26 composed of a plurality of thin film batteries 5. As electrically insulating glue for this purpose, use may be made of ABLEBOND 958-11 from Sikema AB. For connecting and disconnecting the unit, there is a switch 27 which, with conductors 28,29, is connected to the terminal 23 and negative connection 30, respectively, of the composite thin film battery 26. The positive connection 25 is, by the intermediary of a contact element 35 projecting from the battery 26, electrically connected to the contact element 24 of the second batch. For recharging, there is a recharge terminal 31 with associated conductors 32,38.

As an alternative to the electrically insulating glue employed in FIGS. 6a and 6b use is made, in certain applications, of a generally thin electrically insulating film of plastic material, for example polyethylene or the like, which is fixed, e.g. fused to the surface of the electrically conductive polymer layer 20 turned to face towards the heating unit 19. As a rule, the film of plastic material covers the entire major surface of the polymer layer 20. In the embodiments in which the composite battery 26 needs protection against moisture (water vapor or water) the film fixed to the heating unit 19 is generally bonded (e.g. welded or glued) with the protective material which surrounds other parts of the composite battery 26. Hereby, the polymer portion forms a part of the protective sealing of the battery, at the same time as the thermal generation of the polymer increases the usable proportion of the energy power content of the battery. In addition, this embodiment makes it possible for the thermal generating portion of the heating device to be placed in the immediate vicinity of that body or that space which is to be heated.

A major advantage inherent in this embodiment is that the aggregate 33 formed from the heating unit 19 and the thin film battery 26 is suitable for mass production in running series for later cutting into units. After the cutting operation, the cut part is generally enclosed in an electrically insulating casing which also protects against water and water vapour.

Figure 7B:
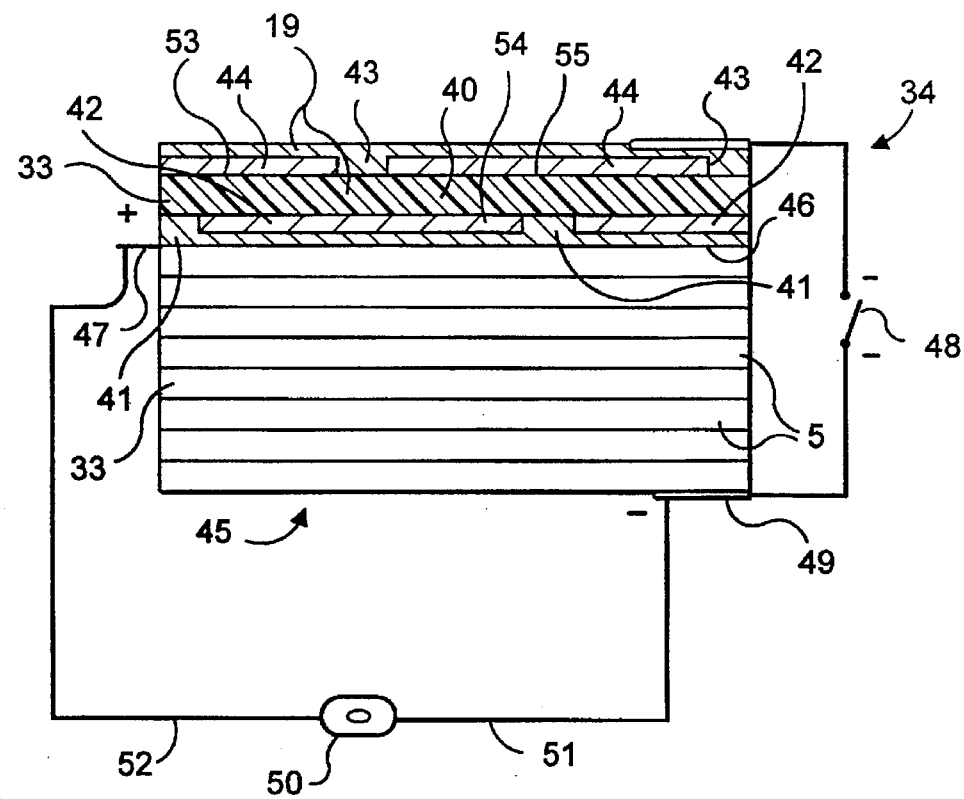

FIGS. 7a and 7b show yet a further embodiment of a heating device 34 in which is included the heating unit 19 formed by the electrically conductive polymer layer 40 and a number of mutually adjacent thin film batteries 5 forming a composite thin film battery 45. In this case, the current is passed through the polymer layer 40 substantially parallel with the two defining surfaces 54,55 of the polymer layer from the first defining surface 54 to the second defining surface 55 of the polymer layer 40. This is achieved in that one or more electrode bands 41 and 43, respectively, abut against the first defining surface 54 and second defining surface 55, respectively, of the polymer layer 40. When more than one electrode band 41,43 abuts against any of the defining surfaces 54,55, the electrode bands are, as a rule, separated at each such surface by electrically insulating layers 42,44 which extend between mutually adjacent electrodes. The surfaces 54,55 of the polymer layer 40 are thereby electrically insulated between the electrode bands 41,43. The insulating layers 42 and 44 are provided so as to prevent electron migration transversly through the polymer down to the conductive layer of the composite thin film battery 45. Instead, the sought-for more horizontally directed current will be obtained through the polymer, which gives uniform heat.

The thin film battery pack 45 has its positive pole 46 combined with the polymer layer 40 so that electric contact exists between the electrode band or electrode bands 41, respectively, and the positive pole layer 46 at the battery pack. The positive pole layer 46 is provided with a projecting contact strip 47. As will be apparent from FIG. 7b the electrode band or the electrode bands 43, respectively, are, via a switch 48, connected to the negative pole 49 of the thin film battery 45. In order to make possible recharge, there is disposed a recharge terminal 50 which, with conductors 51,52 is connected to the negative pole 49 and the contact plate 47, respectively, projecting from the positive pole 46.

As material for the polymer layer 40, use is advantageously made in this embodiment of an electrically conductive plastic ET-Semicon with the type designation CT 6422:70 or CT 6002:70. Application of the electrode bands 41,43 is, for example, effected using a technique corresponding to that described in the foregoing, for example by screen printing, gluing or vacuum coating. In order to electrically connect the individually electrode bands 43 to one another, preferably the entire outside of the resistor unit 40 is covered with a generally thin electrode layer 53. Also the whole of the inside of the polymer material 40 is, in certain embodiments, coated with thin electrically conductive material.

In certain practical applications, in the embodiment illustrated in FIGS. 7a and 7b, a generally thin electrically insulating film of plastic material, for example polyethylene or the like, is fixed, for example fused to the surface of the electrically conductive polymer layer 40 facing towards the heating unit 19, while in other embodiments, such film is absent. As a rule, the film of plastic material covers the entire major surface of the polymer layer 40, in which event the positive pole of the battery is electrically connected to the electrodes 41 by a separate lead wiring (not shown in the figures). In those embodiments in which the composite battery 45 needs protection against moisture (water vapor or water) and in which the film occurs, the film bonded to the heating unit 19 is generally joined (e.g. welded or glued) to the protective material which surrounds other parts of the composite battery 45. In embodiments in which the film is absent, moisture protection is obtained in that the casing or housing surrounds both the heating unit 19 and the battery (cf. also FIG. 9 below). Where the film is absent, the above-mentioned lead wiring to the positive pole of the battery is not required. In both of the embodiments, the heat generation of the polymer increases the extractable proportion of the energy power content of the battery. Moreover, this embodiment makes it possible for the heat generating portion of the heating device to be placed in the immediate proximity of that body or that space which is to be heated.

Also in embodiments described in the preceding paragraphs, the aggregate 33 formed by the heating unit 19 and the thin film battery 45 is suitable for mass production on a production line for later cutting into units, in particular in the embodiment in which the insulating plastic layer between the resistor unit and the battery is not employed.

FIGS. 8–9 illustrate various conceivable embodiments and placements of the resistor heating unit 60, the thin film battery 61 and the operating unit 62.

FIG. 8 shows one embodiment in which the polymer layer 60 of the resistor heating unit 19 and the thin film battery 61 are physically interconnected with one another and, in one preferred version, are included in a laminate. The operating unit 62 is disposed at a separate position and electrically connected by the intermediary of conductors 28,29 with the polymer layer 60 and the negative pole 30 of the thin film battery 61, respectively, of the composite unit in which the resistor unit 19 and the thin film battery 61 are included.

In the embodiment illustrated in FIG. 8, an electrically insulating and water-impermeable plastic material layer 67, e.g. a polythene layer, is disposed between the electrically conductive polymer layer 60 of the heating unit 19 and the battery 61 in order to provide a particularly good moisture seal about the battery 61. This plastic material layer 67 is fused with the water and water vapor-impermeable casing 64 which surrounds the remaining portions of the composite battery 61. This design corresponds to the design in FIGS. 6a and 6b, but with the difference that the plastic material layer 67 has been applied onto the pole layers 25, before the electrically conductive polymer layer (or resistor layer) 20 with its conductors 21,22 has been mounted in place. As will be apparent from FIG. 8, the contact element 24 is connected to the positive pole layer 25. Furthermore, the negative pole connection 30 is, via the insulating conductor 29, electrically connected to the operating unit 62 which is also electrically connected to the second connection of the heating unit 19 and, thereby, the contact element 24 via the conductor 28. This version may advantageously be employed where the requirement on mobility is less severe, for example in sole inlays.

FIG. 9 illustrates yet a further embodiment in which the pole layer 65 of the thin film battery 61 is in directly conductive contact with an electrode material layer 66 connected to the electrically conductive polymer layer 60 of the heating unit 19. This combination of thin film battery 61 and heating unit 69 forms, for example, a laminate and is illustrated, in this drawing Figure, enclosed in a moisture-proof and waterproof casing 64. The operating unit 62 is, in FIG. 9, shown as disposed outside the casing 64 and connected with the heating element via the conductors 63.

FIGS. 10a–c show schematic partial sections of combinations of the heating element 1 and thin film batteries 2 designed in accordance with that described in the foregoing. The letter A is taken to signify thermal energy which is in motion in a direction from the heating element 1 and towards a body or a space which is to be heated. In all of FIGS. 10a–c, the heating element 1 is disposed between the thin film battery 2 and the above-mentioned body or space. The combinations illustrated in the figures also include a casing 64 whose one wall 64a is located on that side of the thin film battery 2 which is turned to face away from the body or the space which is to be heated. The other wall 64b of the casing is located on the opposite side of the thin film battery 2. Both of the walls are closely united with one another by means of a closure 70 in the edge region of the thin film battery 2. Both of the walls of 64a,b of the casing are substantially parallel with the major surfaces 36,37 of the thin film battery.

In FIGS. 10a–c the heating element 1, the thin film battery 2 and both walls 64a,b of the casing are shown as disposed in spaced relationship. In certain practical applications, spacer elements (not shown in the figures) are provided for maintaining these spacings, in particular embodiments in which the device is to form a mechanically rigid unit. In other embodiments, for example when the device is included in a garment, the heating element 1, the thin film battery 2 and the walls 64a,b are moveable towards and away from one another while being fixed in relation to one another at regular distances. FIG. 10d shows a partial magnification of the marked region in FIG. 10a. It will be apparent from the partial magnification that the wall 64a of the casing is, in the illustrated embodiment, composed of a metal foil 68 consisting of one or more layers and a plastic layer 69 on either side of the metal foil. The metal foil is preferably coated with the plastic layers.

FIGS. 10a and 10b show embodiments in which the casing 64 in FIG. 10a surrounds only the thin film battery 2 and in which the casing 64 in FIG. 10b surrounds both the thin film battery 2 and the heating element 1.

FIG. 10c shows one embodiment in which a layer 71 of electrically insulating material which, in addition, is impermeable to both moisture and water, is disposed between the heating element 1 and the thin film battery 2. In addition, the material in the layer 71 is of poor thermal insulation or otherwise expressed, good thermal permeability. The wall 64 of the casing is sealingly connected with the layer.

On use of the embodiments described in FIGS. 10a–d, the thermal energy is reflected by the metal foil 68 back towards the battery 2, whereby this receives elevated temperature which, in turn, makes it possible for a greater portion of the energy power content of the battery to be available to be converted into thermal energy in the heating element 1.

In the description of FIGS. 10a–d, use has been made of the general expressions heating element 1 and thin film battery 2. This is hereby taken to signify that the element 1,10,20,40,60 and/or the battery 2,12,26,45,61 as required is disposed in accordance with one of the alternatives described in the foregoing.

When the above-described embodiments of thin film battery 2,5,12, 26,45,61 and the heating unit 19 which, as a rule, include an electrically insulating polymer material located between the thin film battery and the heating unit, are to be produced in the form of long bands, the advantage will be attained that the band constitutes an intermediate product from which is separated portions or part lengths adapted to the requirements of the pertinent practical application. However, it is obvious that not only the length of the separated part is adaptable to the relevant practical application, but also the form of that part which is cut off.

The size of the separated part or the separated portion is adapted in accordance with the power/energy need which the particular application requires. The construction of the present invention entails that it is possible beforehand to determine the desired generated output per surface unit by dimensioning the battery for a given pole voltage (number of partial batteries 5), selecting polymer material with a certain volume resistivity and/or selecting a certain electrode spacing. The layer thickness of the polymer material is also determinative of the power output per surface unit, There will hereby be obtained a predetermined operational time of that device in which the separated part is included, irrespective of the surface area of the separated part. As a rule, the band is provided with a contact plate for electric contact between heating unit, thin film battery and operating unit, in which event the contact plates abut against the positive or negative poles of the thin film battery, The separated part is thereby simply interconnectable with an operating unit 27,48,62, e.g. as described above with particular reference to FIG. 9. After the cutting operation, the cut portion is generally enclosed in an electrically insulating casing which is also water and water vapour proof. Requisite conductors for, for example, the operating unit and battery charger are sealingly lead through the casing.

In the foregoing description, it is disclosed that the aggregate 33 (material) includes a number of strata which are disposed adjacent one another. The expression "disposed adjacent one another" encompasses a multiplicity of embodiments, for example that the strata are continuously interconnected, that they are discontinuously interconnected, that they are laminated, that they are loosely disposed in relation to one another in portions which are followed by sections where they are interconnected with one another, that they are only interconnected with one another at points, that only two layers out of three are interconnected with one another within a given area, that the layers are interconnected with one another in but the edge regions of, for example, a band, that the strata are laid with the major surfaces facing one another about, for example, a body and are kept in place by outer fixing devices, that the strata are compressed in that a surrounding protective casing is wholly or partly evacuated of its gas content, etc.

In the above description, the term thin film battery has been employed. This is taken to signify both rechargeable thin film batteries and non-rechargeable batteries (primary batteries). The type of battery is adapted to suit the particular practical application in which the present invention is employed.

The description and the accompanying drawings show specific orientations of the poles of the thin film batteries. It will be obvious to the skilled reader of the specification that the disclosed orientations merely constitute examples of embodiments and that the thin film batteries in other embodiments have reverse orientation, entailing that the positive and negative poles have changed place.

It will be obvious to the skilled reader that, even if embodiments have been described in the foregoing in which the resistor heating unit 19 consists solely of an electrically conductive polymer layer 1,10,20,40,60, the heating unit 19 is provided, in other embodiments, with more than one electrically conductive polymer layer.

In certain practical applications of the present invention, the device is designed so as to constitute a rigid and mechanically stable unit, for example be designed as a container. In other practical applications, the device is designed so as to form a flexible and bendable unit. Depending upon those requirements placed by the relevant practical application, the device includes material which entails that the thus formed aggregate 33 is bendable, extendable, elastic, resiliently yieldable, mechanically stable etc.

In the above description, use has occasionally been made of such designations as upper, lower, right, left etc. These designations have been employed solely to facilitate presentation of the invention. It will be obvious to a person skilled in the art that the described technique generally permits any optional orientation in space.

The above-detailed description has referred to but a limited number of embodiments of the present invention, but it will be readily perceived by a person skilled in the art that the present invention encompasses a large number of embodiments without departing from the spirit and scope of the appended claims.

We claim:

1. An electric heating device comprising an electric energy source, a resistor heating unit comprising a first material stratum comprising portions of electrically conductive polymer material with PTC properties, said first material stratum having a pair of mutually oppositely arranged major surfaces, in which the polymer material with PTC properties is united with electrode material which electrically connects said electrically conductive polymer material to the energy source, and a regulator unit for regulating current supply to the resistor heating unit, wherein the electric energy source comprises a thin film battery also having a pair of mutually oppositely arranged major surfaces, and wherein said first material stratum is physically connected to said thin film battery such that the energy source and the resistor heating unit form a composed unit in which respectively one each of the major surfaces of said battery and of said first material stratum are turned to face towards one another.

2. The heating device as claimed in claim 1, wherein one pole layer of the thin film battery is in direct contact with the electrode material applied to the one major surface of the electrically conductive polymer material of the first material stratum.

3. The heating device as claimed in claim 1, comprising an electrically insulating material layer disposed between one pole layer of the thin film battery and the adjacent major surface of the polymer material of the first material stratum.

4. The heating device as claimed in claim 1, wherein in said composed unit, at least the thin film battery is moisture sealed in relation to the surroundings of the battery.

5. The heating device as claimed in claim 4, wherein the first stratum and the thin film battery are tightly enclosed in a common casing which is impermeable to water and water vapor.

6. The heating device as claimed in claim, 1, wherein the electrically conductive polymer with PTC properties is at least one of:

a plastic in which an electrically conductive filler is distributed as an electrically resistive network and which, on heating, has the property of expanding under progressive reduction of electric current paths through the electrically resistive network and vice versa, until a stage of self-regulated thermal stability is achieved; and a butyl-inoculated polyethylene plastic which has been rendered electrically conductive by admixture of carbon black.

7. The heating device as claimed in claim 1, wherein the electrically conductive polymer has said electrode material combined therewith by casting, gluing screen pressing or vacuum coating.

8. The heating device as claimed in claim 1, wherein the electrode material consists at least partly of at least one of metallic material or synthetic metal material.

9. The heating device as claimed in claim 1, wherein there is provided, in regions where the first material stratum and the thin film battery form said composed unit, a material layer which reflects thermal energy incoming towards the stratum; said battery being disposed between said material layer reflecting thermal energy and one of: a body; and a space which is heated by the device.

10. The heating device as claimed in claim 1, wherein the electric energy source and the resistor heating unit are enclosed in a textile material.

11. The heating device of claim 1, wherein said electrode material comprises a first batch of electrodes and a second batch of electrodes, said first and second batches of electrodes both being provided at the major surface of said first material stratum facing said thin film battery, said first batch of electrodes being electrically connected to a first pole of said thin film battery arranged at the major surface of said thin film battery facing said material stratum, said second batch of electrodes being electrically connected to a second pole of said thin film battery.

12. The heating device of claim 11, wherein said first material stratum comprises a pair of projecting contact elements each of which is electrically connected respectively with said first and second batches of electrodes, and wherein said thin film battery comprises a projecting contact element electrically connected with the projecting contact element of said first material stratum which is electrically connected with said first batch of electrodes.

13. The heating device of claim 1, further comprising an electrically insulating layer disposed between the mutually facing major surfaces of said battery and of said first material stratum.

14. The heating device of claim 1, wherein said electrode material comprises a first batch of electrodes provided at the major surface of said first material stratum facing said thin film battery and a second batch of electrodes provided at the major surface of said material stratum facing away from said thin film battery, said first batch of electrodes being electrically connected to a first pole of said thin film battery arranged at the major surface of said thin film battery facing said material stratum, said second batch of electrodes being electrically connected to a second pole of said thin film battery.

15. The heating device of claim 14, further comprising electrically insulating layers provided at both major surfaces of said first material stratum disposed between said first and second batches of electrodes.

16. The heating device of claim 15, wherein substantially the entire outside of said first material stratum at the major surface thereof facing away from said thin film battery is covered with an electrode layer electrically connecting said second batch of electrodes.

17. The heating device of claim 15, wherein substantially the entire inside of said first material stratum at the major surface thereof facing towards said thin film battery is covered with an electrode layer electrically connecting said first batch of electrodes.

18. The heating device of claim 15, wherein substantially the entire outside of said first material stratum at the major surface thereof facing away from said thin film battery is covered with an electrode layer electrically connecting said second batch of electrodes, and substantially the entire inside of said first material stratum at the major surface thereof facing towards said thin film battery is covered with an electrode layer electrically connecting said first batch of electrodes.

* * * * *

UNITED STATES PATENT AND TRADEMARK OFFICE
CERTIFICATE OF CORRECTION

PATENT NO. : 5,643,480
DATED : July 1, 1997
INVENTOR(S) : Magnus P.M. Gustavsson, et. al.

It is certified that error appears in the above-identified patent and that said Letters Patent is hereby corrected as shown below:

Title page, item [54] and col. 1, the title should read--ELECTRIC HEATING DEVICE__.

Signed and Sealed this

Thirteenth Day of January, 1998

Attest:

BRUCE LEHMAN

*Attesting Officer*      *Commissioner of Patents and Trademarks*